United States Patent
Jessouroun et al.

(10) Patent No.: US 9,173,931 B2
(45) Date of Patent: Nov. 3, 2015

(54) PROCESS FOR PREPARING POLYSACCHARIDE-PROTEIN CONJUGATE VACCINES

(75) Inventors: Ellen Jessouroun, Rio de Janeiro (BR); Ivna Alana Freitas Brasileiro Da Silveira, Rio de Janeiro (BR); Renata Chagas Bastos, Rio de Janeiro (BR); Carl E. Frasch, Rockville, MD (US); Che-Hung Robert Lee, Silver Spring, MD (US)

(73) Assignees: The United States of America, as represented by the Secretary, Department of Health and Human Services, Washington, DC (US); Fiocruz, Rio de Janiero (BR)

( * ) Notice: Subject to any disclaimer, the term of this patent is extended or adjusted under 35 U.S.C. 154(b) by 723 days.

(21) Appl. No.: 10/566,898

(22) PCT Filed: Aug. 6, 2004

(86) PCT No.: PCT/US2004/026431
§ 371 (c)(1),
(2), (4) Date: Oct. 26, 2006

(87) PCT Pub. No.: WO2005/037320
PCT Pub. Date: Apr. 28, 2005

(65) Prior Publication Data
US 2007/0110762 A1 May 17, 2007

Related U.S. Application Data
(60) Provisional application No. 60/493,389, filed on Aug. 6, 2003.

(51) Int. Cl.
| A61K 39/095 | (2006.01) |
| A61K 39/385 | (2006.01) |
| A61K 47/48  | (2006.01) |
| A61K 39/09  | (2006.01) |
| A61K 39/00  | (2006.01) |

(52) U.S. Cl.
CPC ............ *A61K 39/095* (2013.01); *A61K 39/385* (2013.01); *A61K 47/4833* (2013.01); *A61K 39/09* (2013.01); *A61K 2039/6037* (2013.01); *A61K 2039/62* (2013.01)

(58) Field of Classification Search
CPC ........ A61K 39/00; A61K 39/02; A61K 39/09
USPC ....................... 424/234.1, 244.1, 258.1, 260.1
See application file for complete search history.

(56) References Cited

U.S. PATENT DOCUMENTS

| 4,356,170 A | | 10/1982 | Jennings et al. |
| 4,963,232 A | * | 10/1990 | Kuriyama et al. ............... 203/29 |
| 5,066,408 A | * | 11/1991 | Powell ........................... 210/765 |
| 5,480,643 A | * | 1/1996 | Donovan et al. .............. 424/409 |
| 5,773,007 A | * | 6/1998 | Penney et al. ............. 424/197.11 |
| 5,849,301 A | * | 12/1998 | Lees ........................... 424/194.1 |
| 5,965,714 A | * | 10/1999 | Ryall ............................. 530/402 |
| 6,756,040 B2 | * | 6/2004 | Peetermans et al. ........ 424/201.1 |
| 6,800,728 B2 | * | 10/2004 | Schwartz ....................... 530/345 |

FOREIGN PATENT DOCUMENTS

WO   WO 2005/014037 A2   2/2005

OTHER PUBLICATIONS

A. E. Tutton Nature 1891 No. 1105 vol. 43 pp. 205-210.*
Behr et al 2003 Tetrahedron 59 pp. 543-553.*
Bartoloni, A. et al. 1995 "Immunogenicity of meningococcal B polysaccharide conjugated to tetanus toxoid or CRM197 via adipic acid dihydrazide" *Vaccine* 13:463-470.
Guo, Z. and Jennings, H. 2001 "Protein-polysaccharide conjugation" In *Methods in Molecular Medicine, Meningococcal Vaccines: Methods and Protocols*, Eds. Pollard, A.J. and Maiden, M.C.J., Humana Press Inc., Totowa, N.J. 66:49-54.
Jennings, H. and Lugowski, C. 1981 "Immunochemistry of groups A, B, and C meningococcal polysaccharide-tetanus toxoid conjugates" *J. Immunol.* 127:1011-1018.
Konadu, E. et al. 2000 "Phase 1 and 2 studies of *Salmonella enterica* serovar *Paratyphi* A O-specific polysacchaaride-tetanus toxoid conjugates in adults, teenagers, and 2- to 4-year-old children in Vietnam" *Infect. Immun.* 68:1529-1534.
Lee, C.-J. 2002 "Quality control of polyvalent pneumococcal polysaccharide-protein conjugate vaccine by nephelometry" *Biologicals* 30:97-103.
Lees, A. et al. 1996 "Activation of soluble polysaccharides with 1-cyano-4-dimethylaminopyridinium tetrafluoroborate for use in protein-polysaccharide conjugate vaccines and immunological reagents" *Vaccine* 14:190-198.
Mulard, L. et al. 2002 "Vaccins polyosidiques" *Ann. L'Institut Pasteur Act.* 12 :37-54.
Shafer, D. et al. 2000 "Activation of soluble polysaccharides with 1-cyano-4-dimethylaminopyridinium tetrafluoroborate (CDAP) for use in protein-polysaccharide conjugate vaccines and immunological reagents. II. Selective crosslinking of proteins to CDAP-activated polysaccharides" *Vaccine* 18:1273-1281.
Communication from European Patent Office Pursuant to Article 94(3) EPC, Dated Jan. 17, 2008 in EP Application No. 04809568.1-2402.

* cited by examiner

*Primary Examiner* — Rodney P Swartz
(74) *Attorney, Agent, or Firm* — Caesar Rivise, PC

(57) ABSTRACT

Methods for the manufacture of polysaccharide-protein conjugate vaccines at high yield are provided. The methods involve reaction of a hydrazide group on one reactant with an aldehyde group on the other reactant. The reaction proceeds rapidly with a high conjugation efficiency. Simplified purification processes can be employed to separate the conjugate product from the unconjugated protein and polysaccharide and other small molecule by-products.

14 Claims, 3 Drawing Sheets

PROCESS FOR PREPARING POLYSACCHARIDE-PROTEIN CONJUGATE VACCINES

CROSS-REFERENCE TO RELATED APPLICATIONS

This application claims the benefit under 35 U.S.C. 119(e) of U.S. Provisional Patent Application No. 60/493,389, filed Aug. 6, 2003.

FIELD OF THE INVENTION

Methods for the manufacture of polysaccharide-protein conjugate vaccines at high yield are provided. The methods involve reaction of a hydrazide group on one reactant with an aldehyde group on the other reactant. The reaction proceeds rapidly with a high conjugation efficiency. Simplified purification processes can be employed to separate the conjugate product from the unconjugated protein and polysaccharide and other small molecule by-products.

BACKGROUND OF THE INVENTION

Bacterial polysaccharides (PSs) are T-independent antigens inducing short-term immunity in older children and adults, but frequently not in young infants. PSs are incapable of binding to the major histocompatibility complex molecules, which is required for antigen presentation to and stimulation of T-helper lymphocytes. PSs are able to stimulate B lymphocytes for antibody production without the help of T-helper lymphocytes. As a result of the T-independent stimulation of the B lymphocytes, there is a lack of memory induction following immunization by these antigens.

T-independent polysaccharide antigens can be converted to T-dependent antigens by covalent attachment of the polysaccharides to protein molecules. B cells that bind the polysaccharide component of the conjugate vaccine can be activated by helper T cells specific for peptides that are a part of the conjugated carrier protein. The T-helper response to the carrier protein serves to augment the antibody production to the polysaccharide. PS-conjugate vaccines are polysaccharide-protein hybrids formed by the covalent attachment of a protein to a PS. Chemical modification of the PS prior to attachment is typically required because most native bacterial PSs cannot be chemically linked to a protein without first undergoing some chemical modification ("activation").

Attachment to the protein yields a number of T cell epitopes. These T cell epitopes interact with CD4 helper T cells, greatly facilitating an antibody response to the attached polysaccharide. The T helper cell-dependent response to a conjugate results in both serum IgG antibodies and immune memory, even in infants. Additionally, the immunogenicity of the PS-conjugate, in contrast to the native PS, is less dependent on the size of the conjugated PS. Accordingly, conjugates prepared with either PS or oligosaccharides can have similar immunogenicity.

There are many conjugation reactions that have been employed for covalently linking polysaccharides to proteins. Three of the more commonly employed methods include: 1) reductive amination, wherein the aldehyde or ketone group on one component of the reaction reacts with the amino or hydrazide group on the other component, and the C=N double bond formed is subsequently reduced to C—N single bond by a reducing agent; 2) cyanylation conjugation, wherein the polysaccharide is activated either by cyanogens bromide (CNBr) or by 1-cyano-4-dimethylammoniumpyridinium tetrafluoroborate (CDAP) to introduce a cyanate group to the hydroxyl group, which forms a covalent bond to the amino or hydrazide group upon addition of the protein component; and 3) a carbodiimide reaction, wherein carbodiimide activates the carboxyl group on one component of the conjugation reaction, and the activated carbonyl group reacts with the amino or hydrazide group on the other component. These reactions are also frequently employed to activate the components of the conjugate prior to the conjugation reaction.

The *Haemophilus influenzae* type b (Hib) conjugate vaccines represent the first PS-protein conjugate vaccines produced for clinical use. Robbins and his colleagues in 1980 utilized the biotechnological process of chemically attaching saccharides to protein carriers, a concept developed 50 years earlier. See Avery et al., J. Exp. Med. 1929; 50:533-550; Schneerson et al., J. Exp. Med 1980; 152:361-376. There are now four different Hib conjugate vaccines licensed in the United States, each different, and each having their own physical, chemical, and immunological characteristics, as summarized in Table 1. A detailed review of the conjugation chemistry and quality control used in these vaccines has been published. See Kniskern et al., "Conjugation: design, chemistry, and analysis" in Ellis et al., Development and clinical uses of *Haemophilus* b conjugate vaccines. New York: Marcel Dekker, 1994: 37-69.

TABLE 1

| Vaccine* | Saccharide size | Carrier protein | Spacer (linker) |
| --- | --- | --- | --- |
| PRP-D (Connaught) | Polysaccharide | Diphtheria toxoid | 6-carbon spacer (ADH) |
| HbOC (Wyeth-Lederle) | Oligosaccharide | Diphtheria protein (CRM) | None (amide) |
| PRP-OMPC (Merck) | Small polysaccharide | Meningococcal protein | Thioether (bigeneric) |
| PRP-T (Aventis Pasteur) | polysaccharide | Tetanus toxoid | 6-carbon spacer (ADH) |

*The four Hib conjugate vaccines are described commonly in the literature with these acronyms and the responsible manufacturers are in parentheses.

The first commercial Hib conjugate, polyribosylribitol phosphate diphtheria toxoid conjugate (PRP-D), consists of partially size-reduced Hib PS attached through a six-carbon spacer, adipic acid dihydrazide (ADH), to diphtheria toxoid using the procedure of Schneerson et al., J. Exp. Med. 1980; 152:361-376. The ADH derivative of diphtheria toxoid was obtained in this method by reaction with ADH in the presence of 1-[3-(dimethylamino)propyl]-3-ethyl carbodiimide hydrochloride (EDC). The Hib PS was then activated by creating cyanate groups on the hydroxyl groups using CNBr. The activated PS was conjugated to the ADH-toxoid (cyanylation conjugation), but the process created an unstable linkage and the conjugate had solubility problems.

The Robbins conjugation chemistry was later modified such that the ADH spacer is added first to the polysaccharide, which is then conjugated to the purified protein in the presence of EDC (carbodiimide reaction). See Chu et al., Infect. Immun. 1983; 40:245-256; Schneerson et al. Infect. Immun. 1986, 52:519-528. This modification improved the conjugation efficiency and product solubility. The vaccine polyribosylribitol phosphate tetanus protein conjugate (PRP-T) utilizes the improved chemistry to covalently link Hib polysaccharide to tetanus toxoid (see Table 1).

The polyribosylribitol phosphate cross reacting mutant diphtheria toxoid conjugate (PRP-CRM) vaccine, also referred to as *Haernophilus* b oligosaccharide conjugate (HbOC), does not contain Hib PS. Instead, it utilizes oligosaccharides of about 20 repeat units derived by periodate oxidation of the glycol functionality in the ribitol moiety. The oxidized oligosaccharides are then attached directly to $CRM_{197}$ a nontoxic mutant form of diphtheria toxin isolated from cultures of *Corynebacterium diphtheriae* C7 (β197), in the presence of sodium cyanoborohydride (reductive amination). See Anderson et al., J. Immunol. 1989; 142:2464-8; and Anderson, Infect. Immun. 1983, 39:233-238. In this conjugation method, the ratio of oligosaccharide to protein was found to be critical for optimal antibody response. See Kniskern et al., "Conjugation: design, chemistry, and analysis" in Ellis et al., Development and clinical uses of *Haemophilus* b conjugate vaccines. New York: Marcel Dekker, 1994: 37-69; Anderson et al., J. Immunol. 1989; 142:2464-8.

Compared to the other Hib conjugate vaccines, Hib polysaccharide-*Neisseria meningitidis* outer membrane protein complex conjugate vaccine (PRP-OMPC) has a number of unique properties. The protein carrier is not a component of the diphtheria, tetanus, and pertussis (DTP) vaccine, but consists of lipopolysaccharide-depleted meningococcal outer membrane vesicles to which are attached size-reduced Hib PS through a thioether linkage. See Marburg et al., J. Amer. Chem. Soc. 1986; 108:5282-5287; Kniskern et al., "Conjugation: design, chemistry, and analysis" in Ellis et al., Development and clinical uses of *Haemophilus* b conjugate vaccines. New York: Marcel Dekker, 1994: 37-69; Anderson et al., J. Immunol. 1989; 142:2464-8. In this process, separate linkers are attached to both the protein and Hib polysaccharide, followed by fusion of the linkers to form a thioether linkage.

*Neisseria meningitidis* is a leading cause of bacterial meningitis and sepsis throughout the world. Pathogenic meningococci are enveloped by a polysaccharide capsule that is attached to the outer membrane surface of the organism. Thirteen different serogroups of meningococci have been identified on the basis of the immunological specificity of the capsular polysaccharide. See Frasch et. al., 1985. Of these thirteen serogroups, five cause the majority of meningococcal disease; these include serogroups A, B, C, W135, and Y. Serogroup A is responsible for most epidemic disease. Serogroups B, C, and Y cause the majority of endemic disease and localized outbreaks. Host defense of invasive meningococci is dependent upon complement-mediated bacteriolysis, The serum antibodies that are responsible for complement-mediated bacteriolysis are directed in large part against the outer capsular polysaccharide. See Rosenstein et al., N. Engl. J. Med., 344:1378-1388, 2001.

With the exception of serogroup B, polysaccharide safety vaccines that induce age-related protection have been available for many years. However, following polysaccharide vaccines administration, antibodies titers fall rapidly and immunological memory is not induced, See Jodar et al., 2000, Biologicals, 28:193-197.

Conventional vaccines based on meningococcal polysaccharide elicit an immune response against the capsular polysaccharide. These antibodies are capable of complement-mediated bacteriolysis of the serogroup specific meningococci. Meningococcal vaccines containing purified capsular polysaccharides induce protective serum bactericidal antibodies in adults, however they are poorly immunogenic in children below 4 years old and may induce tolerance. See Taunay et al., 1974, Pediatr. Res., 8:429; Gold et al., 1975, J. Clin. Invest., 56: 1536-1547; Leach et al., 1997, J. Infect. Dis., 175:200-204.

To overcome the limitations of polysaccharide vaccines and based on the acknowledged success of conjugate Hib vaccines, recent efforts in the development of meningococcal serogroups A and C glycoconjugate vaccines have been reported. The widespread use of Hib conjugate vaccines also protects age groups not included in vaccination programs through the reduction of carriage state and transmission resulting in herd immunity. See Peltola, H. 2000, Clinical Microbiol. Reviews, 13:302-317. These vaccines have been shown immunogenic and well tolerated in infants. Long-term immunity is improved by induction of memory, as demonstrated for the serogroup C component of meningococcal AC conjugate vaccine administered to Gambian infants. See Fairley et al., 1996, J. Infect. Dis., 174: 1360-1363; Leach et al., 1997, J. Infect. Dis., 175:200-204.

Saccharide-protein conjugate vaccines against *N. meningitidis* serogroups A and C or other encapsulated bacteria have proven to be efficacious in reducing human disease caused by these pathogens. The covalent coupling of bacterial oligo or polysaccharide, which induce T-cell independent immune response, to T-cell dependent protein immunogens results in molecules that are highly immunogenic in infants and young children inducing memory responses. See Chu et al., 1983, Infect. Immun., 40: 245-256; Richmond et al., 1999, J. Infect. Dis., 179:1569-1572; Peltola, H. 2000, Clinical Microbiol. Reviews, 13:302-317; Ramsay et al., 2001, Lancet, 357:195-196.

Over the last 5 years, in the United Kingdom, the incidence of meningococcal disease has increased rapidly, which led to the development of meningococcal C conjugate vaccine to be applied in immunization programs for all children aged from 1 to 18 years. After proving that a single dose would be sufficient for priming and inducing immunological memory, in 1999, the United Kingdom became the first country to introduce meningococcal vaccines in their national program of immunization. See Department of Health, London, 1999, PL/CMO/99/2 PL/CNO/99/4 PL/CPHO/99/1; Richmond et al., 1999, J. Infect. Dis., 179:1569-1572; Richmond et al., 2001, J. Infect. Dis., 183:160-163.

Infant vaccination with meningococcal conjugates may provide long-term protection against disease. Antibody levels and immunologic memory were assessed in 5-year-old Gambian children who received meningococcal A/C conjugate vaccination (MenA/C) in infancy. See MacLennan et al., 2001, J. Infect. Dis. 183:97-104.

In Brazil, the meningococcal disease occurs in 1-3/100,000 inhabitants, and is mainly caused by serogroup B (60%) followed by serogroup C (40%). See Sifontes et al., 1997, Arch. Med. Res., 28:41-5. To achieve disease control since the seventies, Brazil has been producing polysaccharide vaccines (A/C) against *Neisseria meningitidis*. In order to follow the technological improvement for polysaccharide bacterial vaccines, polysaccharide A-tetanus toxoid and polysaccharide C-tetanus toxoid vaccines have been developed using reductive amination methodology as the starting procedure. See Jennings et al., 1981, J. Immunol., 127: 1011-1018. The selected approach was firstly applied to A and C polysaccharides and has potential applicability to other meningococcal polysaccharides.

There are a number of approaches that have been employed for activation of the meningococcal PS and for conjugation, as summarized in Table 2. Each mode of activation has the potential to alter important epitopes, even when relatively few sites are activated on the PS molecule. Periodate activation of the group C meningococcal PS, for example, results in chain breakage generating smaller saccharide units with terminal aldehyde groups that can be linked to the protein via reductive animation. See Richmond et al., J. Infect. Dis. 1999; 179: 1569-72.

TABLE 2

| Method | Saccharide size | Carrier protein | Spacer | Procedure | Used in humans |
|---|---|---|---|---|---|
| #1 Reductive amination | Reduced | Tetanus toxoid | None | Aldehyde form of PS combined with protein in presence of sodium cyanoborohydride | No |
| #2 Carbodiimide | Native | Tetanus toxoid | None | PS and protein combined in presence of carbodiimide, then blocked with ethanolamine | No |
| #3 Active ester[a] | Oligosaccharide | $CRM_{197}$ | Adipic acid | Aminated reducing terminus of the oligosaccharide conjugated to protein by adipic acid $(NHS)_2$ | Yes |
| #4 Reductive amination | Reduced | $CRM_{197}$ | None | Aldehyde form of saccharide combined with protein in presence of sodium cyanoborohydride | Yes |
| #5 Reductive amination | De-OAc PS[b] | Tetanus toxoid | None | Aldehyde form of PS combined with protein in presence of sodium cyanoborohydride | Yes |

[a]N-hydroxysuccinimide diester of adipic acid
[b]Deacetylylated PS only reported for Meningococcal group C Initial studies on production and optimization of meningococcal group C conjugates were reported well before commercialization of the Hib conjugates. See Beuvery et al., Infect. Immun. 1982; 37:15-22; Beuvery et al., Infect. Immun. 1983; 40:39-45; Beuvery et al., J. Infect, 1983; 6:247-55; Jennings, et al., J. Immunol. 1981; 127:1011-8.

Two different conjugation methodologies have been reported for chemically linking the group C PS to a protein carrier. See Jennings et al., J. Immunol. 1981; 127:1011-8; Beuvery et al., Infect. Immun. 1983; 40:39-45. The first approach employs partially depolymerized PS, which is activated by creation of terminal aldehyde groups through periodate oxidation (Method #1 in Table 2). The aldehydes are then reacted through reductive amination combined with free amino groups on the protein, mostly lysines, in the presence of sodium cyarioborohydride. See Jennings et al., J Immunol 1981; 127:1011-8. In this method, activation occurs at one specific site on the group C PS.

The second approach utilizes the carbodiimide reaction (Method #2 in Table 2) to covalently link carboxylic groups in the high molecular weight PS to lysine a-amino groups on the carrier protein. The activation sites in this method are more random, compared to periodate activation.

Group C meningococcal conjugates prepared by these two methods have been evaluated in animals. See Beuvery et al., Dev. Biol. Stand. 1986; 65:197-204; and Beuvery et al., J. Infect. 1983; 6:247-55. The conjugates stimulated both T cell independent and T cell dependent responses upon initial immunization. See Beuvery et al., J. Infect. 1983; 6:247-55. Studies have shown that the PS must, however, be covalently linked to the carrier protein to induce a T cell dependent antibody response.

The first group A and group C meningococcal conjugates to be used in clinical trials were prepared by Chiron Vaccines and were reported in 1992 (Method #3 in Table 2). See Costantino et al., Vaccine 1992; 10:691-8. The conjugation method was based upon selective terminal group activation of small oligosaccharides produced by mild acid hydrolysis followed by coupling to a protein through a hydrocarbon spacer. The non-toxic mutant of diphtheria toxin, $CRM_{197}$, was used as the protein carrier. To activate the oligosaccharides for conjugation, an amino group was added to the end of the oligosaccharide, and then reacted with the N-hydroxysuccinimide diester of adipic acid to create an active ester. This active ester was then covalently bound to lysine a-amino groups in the $CRM_{197}$ protein, creating the conjugate.

SUMMARY OF THE INVENTION

Conventional methods for the preparation of PS-protein conjugate vaccines do not use hydrazide chemistry in the reductive amination conjugation reaction, even though hydrazide in the form of ADH has been used in activating polysaccharide. These prior art methods utilize ϵ-amino groups of lysine residues on the protein to react with functional groups on activated PSs, such as aldehyde groups (reductive amination) and carboxyl groups. The efficiency of the reaction is low, typically only about 20%. The reaction also requires two to three days for the conjugation to be completed, necessitating the use of purification steps to separate the conjugate from unreacted PS. See Guo et al., "Protein-polysaccharide conjugation" in: Pollard et al., Methods in Molecular Medicine, Vol. 66: Meningococcal Vaccines: methods and Protocols, Humana Press, Totowa, N.J., 2001, pg 49-54. There are a number of explanations that have been proposed for the low yields observed. First, the e-amino group of lysine (pKa=10.5) has low reactivity at the conjugation conditions (pH 6.5-7.4). See Inman et al., Biochemistry 1969; 8:4074-4082. Secondly, most conjugation methods employ toxoids as the carrier proteins. The toxoids are derived from a toxin by detoxification with formaldehyde, which combines with the amino groups of the toxin, leaving a limited numbers of amino groups available for conjugation. Thirdly, reduced solubility of the resulting activated protein and protein-PS conjugate can lead to precipitation.

Existing vaccines based on PSs are of limited use in young children and do not provide long-lasting protection in adults. Thus, a need exists for a protein-PS conjugate vaccine capable of conferring long term protection against diseases in children and adults at risk for, e.g., bacterial meningitis, influenza, tetanus, and other bacterial infections. The protein-PS conjugates of the preferred embodiment can be employed to prepare vaccine formulations capable of conferring long term protection to infants, children, and adults.

Accordingly, methods for the manufacture of polysaccharide-protein conjugate vaccines in high yields are desirable. Also desirable are methods wherein the reaction proceeds at a rapid rate, with reduced production of undesired by-products, and with reduced amounts of unreacted protein and polysaccharide remaining at the end of the reaction.

A scaled-up procedure for the production of commercial volumes (from 8 mL to 2,000 mL or more of final product) is provided including purification equipment optimization. During the methodology standardization, the immunogenic potential of the Men C conjugates was compared to plain CPS in mice through total antibody induction by ELISA, and their bactericidal activity was against *N. meningitidis* C strain. In this methodology, the polysaccharides A (APS) and C (CPS) from *N. meningitidis* produced in Bio-Manguinhos, Fiocruz, Rio de Janeiro, Brazil, were covalently linked to tetanus toxoid (TT) (from Instituto Butantan, Sao Paulo, Brasil), by reductive amination in presence of sodium cyanoborohydride. TT was activated with hydrazine dihydrochloride in excess, to introduce hydrazine (—$NH_2$—$NH_2$) groups by carbodiimide reaction.

Accordingly, in a first embodiment, a method for preparing a conjugate vaccine is provided, the method comprising reacting a polysaccharide with an oxidizing agent, whereby a solution of an aldehyde-activated polysaccharide is obtained; reacting a protein with hydrazine dichloride at an acidic pH, whereby a solution of a hydrazine-activated protein is obtained; reacting the aldehyde-activated polysaccharide with the hydrazine-activated protein at a pH of from about 5 to about 7 in the presence of sodium cyanoborohydride, whereby a conjugate is obtained; and neutralizing unreacted aldehyde groups with adipic acid dihydrazide, whereby a conjugate vaccine capable of stimulating an immune response is obtained.

In an aspect of the first embodiment, the oxidizing agent comprises $NaIO_4$.

In an aspect of the first embodiment, the solution of the aldehyde-activated polysaccharide is buffer exchanged with a HEPES buffer.

In an aspect of the first embodiment, the solution of the aldehyde-activated polysaccharide is buffer exchanged to a pH of from about 7 to about 8

In an aspect of the first embodiment, the solution of the hydrazine-activated protein is buffer exchanged with a $Na_2CO_3$ buffer.

In an aspect of the first embodiment, the solution of the hydrazine-activated protein is buffer exchanged to a pH of from about 10.0 to about 11.0.

In an aspect of the first embodiment, a pH of the solution of the hydrazine-activated protein is raised to from about 7.0 to about 11 before the solution of the hydrazine-activated protein is buffer exchanged to a pH of from about 10.0 to about 11.0.

In an aspect of the first embodiment, the aldehyde-activated polysaccharide is reacted with the hydrazine-activated protein at a ratio of from about 1:1.6 to about 1:5.

In an aspect of the first embodiment, the method further comprises the step of diafiltrating the conjugate vaccine, whereby substantially all unreacted compounds and unconjugated polysaccharides are removed, yielding a purified conjugate vaccine.

In an aspect of the first embodiment, the method further comprises the step of concentrating the purified conjugate vaccine by tangential flow ultrafiltration, yielding a concentrated purified conjugate vaccine.

In an aspect of the first embodiment, the method further comprises the step of adding saccharose as a stabilizer to the concentrated purified conjugate vaccine, yielding a stabilized conjugate vaccine.

In an aspect of the first embodiment, the method further comprises the step of freeze drying the concentrated purified conjugate vaccine, yielding a dried conjugate vaccine.

In an aspect of the first embodiment, the polysaccharide is selected from the group consisting of *Meningococcal polysaccharides, Pneumococcus polysaccharides, Hemophilus influenzae* type b polysaccharide, Vi polysaccharide of *Salmonnella typhi*, and group B *Streptococcus polysaccharides*.

In an aspect of the first embodiment, the protein is selected from the group consisting of tetanus toxoid, diptheria toxoid, $CRM_{197}$, and meningococcal protein.

DETAILED DESCRIPTION OF THE PREFERRED EMBODIMENT

Figure 1:
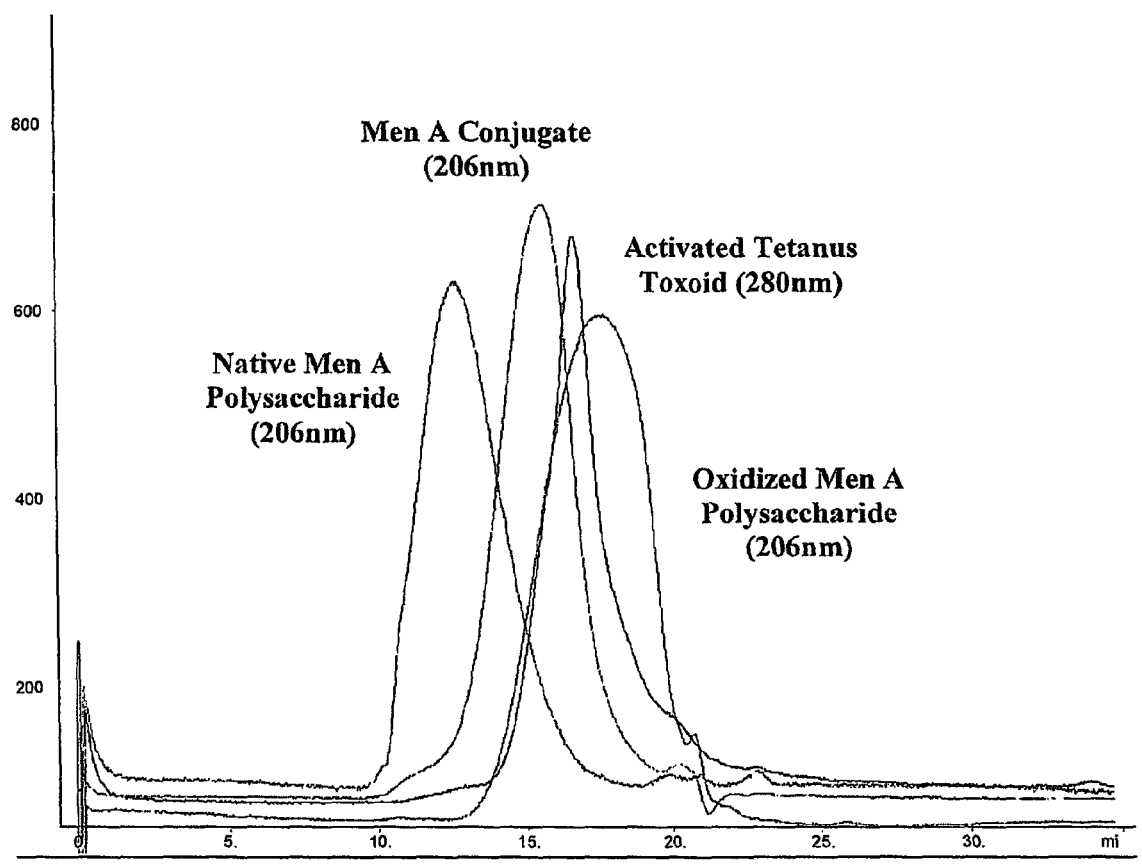
FIG. 1 provides high performance liquid size-exclusion chromatography (HPSEC) profiles of native and oxidized Men A polysaccharides, Men A conjugate and activated tetanus toxoid.

The following description and examples illustrate a preferred embodiment of the present invention in detail. Those of skill in the art recognize that there are numerous variations and modifications of this invention that are encompassed by its scope. Accordingly, the description of a preferred embodiment should not be deemed to limit the scope of the present invention.

Introduction

Conventional methods for synthesis and manufacturing of polysaccharide-protein conjugate vaccines typically employ conjugation reactions with low efficiency (typically about 20%). This means that up to 80% of the added activated polysaccharide is lost. In addition, a chromatographic process for purification of the conjugates from unconjugated PS is typically required. The synthetic methods of the preferred embodiments utilize the characteristic chemical property of hydrazide groups on one reactant to react with aldehyde groups or cyanate esters on the other reactant with an improved conjugate yield (typically as high as about 60%).

When the conjugation reaction proceeds with a greater conjugation efficiency, the amount of unconjugated protein and polysaccharide remaining after reaction can be sufficiently low so as to make its removal unnecessary. Accordingly, the process of purifying the conjugate product can be simplified to, e.g., a diafiltration step for removal of small molecule by-products. The hydrazide-based conjugation reaction can be carried to completion within one or two days at reactant concentrations of from about 1 to about 40 mg/mL at PS/protein mole ratios of from about 1:5 to about 5:1, preferably from about 1:2 to about 1:1.6 or 1:1, although in certain embodiments higher or lower ratios can be preferred. The conjugation reaction is preferably conducted at temperatures of from about 4° C. to about 40° C., preferably from about 5, 10, 15, or 20° C. to about 25, 30, or 35° C., and at a pH of from about 6 to about 8.5, preferably from about 6.1, 6.2, 6.3, 6.4, or 6.5 to about 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, or 8.4, with optimal conditions varying according to the polysaccharide. Accordingly, conjugate vaccine can be manufactured at lower cost when a hydrazide-based conjugation reaction is employed.

To overcome certain drawbacks of conventional methods for synthesizing conjugate vaccines, a method for conjugation of PSs to carrier proteins using hydrazide chemistry in reduction amination and cyanylation conjugation reactions is provided. Hydrazide groups having the structure —NH—$NH_2$ are introduced onto the carboxyl groups of the aspartic acid and/or glutamic acid residues of protein molecules by carbodiimide reaction with hydrazine, ADH, carbohydrazide, or succinyl dihydride. The activated protein is maintained soluble at a pH of from about 10 to about 11.5, preferably from about 10.1, 10.2, 10.3, or 10.4 to about 10.6, 10.7, 10.8, 10.9, 11.0, 11.1, 11.2, 11.3, or 11.4, and most preferably about 10.5, with a buffer at a concentration of from about 3 or less to about 10 mM or more, preferably from about 4 or 5 mM to about 6, 7, 8, or 9 mM, before conjugation. Suitable buffers include but are not limited to $Na_2CO_3$, 3-(cyclohexylamino)-1-propanesulfonicacid (CAPS), and (2-cyclohexylamino)ethane sulfonic acid (CHES). The activated protein is then reacted with activated polysaccharide containing either aldehyde (reductive amination) or cyanate (cyanylation conjugation) groups at a pH of from about 6 to about 8.5, preferably from about 6.1, 6.2, 6.3, 6.4, or 6.5 to about 6.6, 6.7, 6.8, 6.9, 7.0, 7.1, 7.2, 7.3, 7.4, 7.5, 7.6, 7.7, 7.8, 7.9, 8.0 in the presence of a buffer at a concentration about 100 mM or less to about 200 mM, preferably from about 110, 120, 130, 140 or 150 mM to about 160, 170, 180 or 190 mM. Suitable buffers include but are not limited to N-(2-hydroxyethyl) piperazine-N'-(2-ethanesulfonic acid) (HEPES), phosphate buffered saline (PBS), TES (EDTA, Tris-HCl, SDS), morpholinopropanesulfonic acid (MOPS), and N,N-bis(2-hydroxyethyl)-2-aminoethanesulfonic acid (BES).

Alternatively, the PS can be functionalized with hydrazide groups. The activated PS can be conjugated, at pH 6.5-7.5 with a strong buffer, to activated proteins containing aldehyde groups (reductive amination). The protein is maintained soluble at a pH of about 10.5 with a weak buffer until the point of conjugation. Because of the higher reactivity of hydrazide groups (pKa=2.6) compared to the lysine ε-amino group (pKa=10.5) at neutral/mild acidic conditions, and the enhanced solubility of the conjugate using activated protein maintained soluble at about pH 10.5 before conjugation, the yield of the conjugation reaction is greatly increased.

Conjugates prepared by these methods are immunogenic in experimental animals, as demonstrated in experiments on mice. In addition, the conjugation reaction can be efficiently carried out without sodium cyanoborohydride, thereby avoiding introduction of cyanide ion in the conjugate product. The reaction can be conducted under mild acidic or neutral pH conditions at room temperature or at 4° C. overnight as opposed to days for conventional reductive amination conjugation methods. This again ensures high yield conjugate vaccine production for unstable polysaccharides, such as those from *Haemophilus influenzae* type b, *Streptococcus pneumoniae* type 19F and *Neisseria meningitides* group A. The methods of preferred embodiments can be employed to produce less expensive conjugate vaccines, thereby greatly promoting public health.

The Polysaccharide

"The term "polysaccharide" as used herein, is a broad term and is used in its ordinary sense, including, without limitation, saccharides comprising a plurality of repeating units, including, but not limited to polysaccharides having 50 or more repeat units, and oligosaccharides having 50 or less repeating units. Typically, polysaccharides have from about 50, 55, 60, 65, 70, 75, 80, 85, 90, or 95 repeating units to about 2,000 or more repeating units, and preferably from about 100, 150, 200, 250, 300, 350, 400, 500, 600, 700, 800, 900 or 1000 repeating units to about, 1100, 1200, 1300, 1400, 1500, 1600, 1700, 1800, or 1900 repeating unit. Oligosaccharides typically about from about 6, 7, 8, 9, or 10 repeating units to about 15, 20, 25, 30, or 35 to about 40 or 45 repeating units.

Suitable polysaccharides for use in the preferred embodiments include polysaccharides and oligosaccharides from encapsulated bacteria The polysaccharides and oligosaccharides can be from any source, for example, they can be derived from naturally-occurring bacteria, genetically engineered bacteria, or can be produced synthetically. The polysaccharides and oligosaccharides can be subjected to one or more processing steps prior to activation, for example, purification, functionalization, depolymerization using mild oxidative conditions, deacetylation, and the like. Post processing steps can also be employed, if desired. Any suitable method known in the art for synthesizing, preparing, and/or purifying suitable polysaccharides and oligosaccharides can be employed.

Polysaccharides and oligosaccharides for use in preferred embodiments include pneumococcal polysaccharides of, for example, serotypes 1, 2, 3, 4, 5, 6B, 7F, 8, 9N, 9V, 10A, 11A, 12F, 14, 15B, 17F, 18C, 19A, 19F, 20, 22F, 23F and 33F; meningococcal polysaccharides of serotypes A, B, C, W135, and Y, *Haemophilus influenzae* type b polysaccharide polyribosylribitol phosphate, group B streptococcal polysaccharides of serotypes III and V and *Salmonella typhi* Vi polysaccharide. Other polysaccharides of pneuinococcal and group B streptococcal serotypes, and meningococcal serogroups are also suitable for use herein, as are other T-independent polysaccharide and oligosaccharide antigens, for example, polysaccharides or oligosaccharides derived from group A streptococcus, *Staphylococci, Enterococci, Klebsiella pneumoniae, E. coli, Pseudomonas aeruginosa*, and *Bacillus anthracis*. While bacterial polysaccharides and oligosaccharides are particularly preferred, gram (−) bacterial lipopolysaccharides and lipooligosaccharides and their polysaccharide and oligosaccharide derivatives, and viral polysaccharides and oligosaccharides can also be employed.

Polysaccharides with side chain phosphorus and/or backbone phosphorus are suitable for use in preferred embodiments. The conjugation reactions of preferred embodiments are particularly well suited for use with polysaccharides having phosphorus in the backbone. Such polysaccharides are sensitive to fragmentation and degradation, so the rapidity of the conjugation reaction results in a higher quality conjugate due to the reduced time during which degradation can occur.

After completion of any pre-processing steps, the polysaccharide or oligosaccharide is subjected to an "activation" step. The term "activation" refers to a chemical treatment of the polysaccharide to provide chemical groups capable of reacting with the protein. In a particularly preferred embodiment, activation involves functionalization of the polysaccharide or oligosaccharide with hydrazide groups that are reacted with aldehyde groups on a functionalized protein. Alternatively, the polysaccharide or oligosaccharide can be functionalized with aldehyde groups, ketone groups, or cyanate groups that are reacted with hydrazide groups on a functionalized protein.

Any suitable functionalization reaction can be employed to activate the polysaccharide or oligosaccharide with hydrazide groups. A preferred functionalization reaction is reductive amination, wherein the polysaccharide or oligosaccharide is reacted with $NaIO_4$ in a periodate activation reaction to yield aldehyde groups, which are then reacted with adipic acid dihydrazide, followed by subsequent reduction with $NaBH_4$.

Any suitable functionalization reaction can be employed to activate the polysaccharide or oligosaccharide with aldehyde groups. Certain polysaccharides and oligosaccharides possess terminal aldehyde groups that can participate in the conjugation reaction. If the polysaccharide or oligosaccharide is activated with aldehyde groups, a preferred reaction involves reaction with an oxidizing agent, such as $NaIO_4$. Oxidizing agents have the potential for fragmenting the polysaccharide or oligosaccharide. Undesirable fragmentation can be avoided or controlled through selection of the particular oxidizing agent and the concentration of the oxidizing agent employed. Ketone groups are also capable of reacting with hydrazide, so activated of the polysaccharide or oligosaccharide with ketone groups can be employed in certain embodiments.

A strongly buffered (at pH of from about 6.5 to about 8, with a high buffer concentration of from about 100 mM to about 200 mM) activated polysaccharide solution is preferably employed in the conjugation reaction in the form of a strongly buffered solution. Any suitable buffer can be employed, preferably a buffer such as N-(2-Hydroxyethyl) piperazine-N'-(2-ethanesulfonic acid).

The Protein

The activated polysaccharide or oligosaccharide is coupled to a protein to yield a conjugate vaccine. Suitable proteins include bacterial toxins that are immunologically effective carriers that have been rendered safe by chemical or genetic means for administration to a subject. Examples include inactivated bacterial toxins such as diphtheria toxoid, $CRM_{197}$, tetanus toxoid, pertussis toxoid, E. coli LT, E. coli ST, and exotoxin A from Pseudomonas aeruginosa. Bacterial outer membrane proteins such as, outer membrane complex c (OMPC), porins, transferrin binding proteins, pneumolysis, pneumococcal surface protein A (PspA), pneumococcal adhesin protein (PsaA), or pneumococcal surface proteins BVH-3 and BVH-11 can also be used. Other proteins, such as protective antigen (PA) of Bacillus anthracis, ovalbumin, keyhole limpet hemocyanin (KLH), human serum albumin, bovine serum albumin (BSA) and purified protein derivative of tuberculin (PPD) can also be used. The proteins are preferably proteins that are non-toxic and non-reactogenic and obtainable in sufficient amount and purity that are amenable to the conjugation methods of preferred embodiments. For example, diphtheria toxin can be purified from cultures of Corynebacteria diphtheriae and chemically detoxified using formaldehyde to yield a suitable protein.

Fragments of the native toxins or toxoids, which contain at least one T-cell epitope, are also useful, as are outer membrane protein complexes, as well as certain analogs, fragments, and/or analog fragments of the various proteins listed above. The proteins can be obtained from natural sources, can be produced by recombinant technology, or by synthetic methods as are known in the art. Analogs can be obtained by various means, for example, certain amino acids can be substituted for other amino acids in a protein without appreciable loss of interactive binding capacity with structures such as, for example, antigen-binding regions of antibodies or binding sites on substrate molecules. Other proteins can also be employed, such as those containing surface exposed glutamic acid or aspartic acid groups.

Any suitable functionalization reaction can be employed to activate the protein with hydrazide groups. Preferably, hydrazide groups are introduced into proteins through the carboxyl groups of aspartic acid and glutamic acid residues on the protein using a carbodiimide reaction, for example, by reaction with hydrazine, carbohydrazide, succinyl dihydrazide, adipic acid dihydrazide or any other dihydrazides in the presence of EDC. EDC is employed as a catalyst to activate and modify the protein reactant with hydrazine or the dihydrazide. Any water-soluble carbodiimide including EDC can be used as a catalyst. EDC-catalyzed proteins generally have a tendency to polymerize and precipitate, and thus are generally not preferred for preparation of conjugates involved with protein. See Schneerson et al., Infect. Immun. 1986, 52:519-528; Shafer et al., Vaccine 2000; 18(13): 1273-1281; and Inman et al., Biochemistry 1969; 8:4074-4082. Aggregation and precipitation of the activated protein depends, in part, on its pH environment. Accordingly, the tendency to polymerize and precipitate can be controlled by maintaining such hydrazide-modified proteins soluble in a buffered solution. By buffer-exchanging the reaction mixture so as to maintain the activated protein at a pH of about 10.5, the activated protein remains soluble and stable for conjugation. Any suitable buffer can be employed. Preferably a weak buffer such as $Na_2CO_3$ at a low concentration of from about 3 mM to about 10 mM is employed.

The buffered hydrazide-modified protein can then be employed in preparing protein-polysaccharide conjugates without precipitation when added to activated polysaccharide at a pH of from about 6 to 9.5, preferably from about 6.5 to about 8. Any suitable functionalization reaction can be employed to activate the protein with aldehyde groups. Preferably, the protein is reacted with 1-amino-2,3-propanediol in the presence of EDC. Amino sugars such as glucosamine, galactosamine, and the like can be used in place of 1-amino-2,3-propanediol. In this reaction, EDC is also employed as a catalyst to activate and modify the protein reactant with the aminodiol through the carboxyl groups of aspartic acid and glutamic acid residues of the protein.

Preparation of Conjugates by Reductive Amination

Conjugates can be prepared via the reaction of aldehyde and hydrazide groups (reductive amination). The reductive amination conjugation reaction can be employed to conjugate a hydrazide-modified reactant (protein or polysaccharide) to the other component containing aldehyde groups.

In conventional reductive amination, the reaction between aldehyde and amino groups is reversible and unfavorable, such that sodium cyanoborohydride is needed to facilitate the conjugation by converting the C=N double bond to a C—N single bond to render the entire reductive amination event irreversible. In contrast, the reductive amination conjugation reaction of preferred embodiments proceeds without the aid of sodium cyanoborohydride because of the high efficiency of the hydrazide-aldehyde reaction. At the end of the reductive amination conjugation reaction, sodium borohydride or another suitable reactant is employed to reduce the C=N double bond to a C—N single bond, as well as to reduce any residual aldehyde groups to alcohol groups. The reductive amination conjugation reaction of preferred embodiments avoids contamination of the resulting conjugate with cyanide, a by-product of sodium cyanoborohydride.

To reduce precipitation of activated protein during the conjugation reaction, the activated protein is preferably in the form of a weakly buffered solution with a low buffer concentration of from about 3 mM to about 10 mM which is added to a strongly buffered (at pH of from about 6.5 to about 7.5, with a high buffer concentration of from about 100 mM to about 200 mM) activated polysaccharide solution. Preferably, the pH of the activated protein solution is buffered to from about 10 pH to about 11.5 pH, most preferably to about 10.5 pH. The activated polysaccharide solution is preferably strongly buffered to from about 6 pH to about 8 pH, most preferably to from about 6.5 pH to about 7.5 pH. The hydrazide-aldehyde reductive amination reaction proceeds at a fast rate, and the precipitating effect of a pH lower than 10.5 (for example, a pH as low as from about 8.5 to about 9.5) on activated protein is overcome by the molecular properties of the reacting activated polysaccharide.

The Conjugates

Both reactants contain multiple reactive groups per molecule. An activated polysaccharide molecule can react with and form more than one linkage to more than one activated protein molecule. Likewise, an activated protein molecule can react with and form more than one linkage to more than one activated polysaccharide molecule. Therefore, the conjugate product is a mixture of various crosslinked matrix-type lattice structures. For example, a single linkage can be present, or 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more linkages can be present. The average number of linkages between a polysaccharide and a protein can be adjusted, as preferred. The preferred average number of linkages can depend upon the type of polysaccharide, the type of protein, the conjugation method, the reaction conditions, and the like. Generally, an average of 1 linkage to about 2, 3, 4, or 5 linkages is present, so as to avoid interfering with the ability of the protein to stimulate the immune system by over-conjugation, and so as to not cause changes in the polysaccharide structure. However, in certain embodiments more than 5 linkages can be tolerated or even desirable.

After conjugation, the conjugate can be purified by any suitable method. Purification is employed to remove unreacted polysaccharide, protein, or small molecule reaction byproducts. Purification methods include ultrafiltration, size exclusion chromatography, density gradient centrifugation, hydrophobic interaction chromatography, ammonium sulfate fractionation, and the like, as are known in the art. As discussed above, the conjugation reactions of preferred embodiments proceed with higher yield, and generate fewer undesirable small molecule reaction byproducts. Accordingly, no purification may be necessary, or only a minor degree of purification can be desirable. The conjugate can be concentrated or diluted, or processed into any suitable form for use in pharmaceutical compositions, as desired.

Methods of Treatment

Conjugates prepared according to the preferred embodiment are administered to a subject in an immunologically effective dose in a suitable form to treat and/or prevent infectious diseases. The term "subject" as used herein, refers to animals, such as mammals. For example, mammals contemplated include humans, primates, dogs, cats, sheep, cattle, goats, pigs, horses, mice, rats, rabbits, guinea pigs, and the like. The terms "subject", "patient", and "host" are used interchangeably. As used herein, an "immunologically effective" dose of the conjugate vaccine is a dose which is suitable to elicit an immune response. The particular dosage depends upon the age, weight and medical condition of the subject to be treated, as well as on the method of administration. Suitable doses can be readily determined by those of skill in the art.

Pharmaceutical compositions comprising conjugate vaccines of preferred embodiments can offer various advantages over conventional vaccines, including enhanced immunogenicity of weakly immunogenic antigens, potential reduction in the amount of antigen used, less frequent booster immunizations, improved efficacy, preferential stimulation of immunity, or potential targeting of immune responses. The vaccines can be administered to a subject by a variety of routes, as discussed below, including but not limited to parenteral (e.g., by intracisternal injection and infusion techniques), intradermal, transmembranal, transdermal (including topical), intramuscular, intraperitoneal, intravenous, intra-arterial, intralesional, subcutaneous, oral, and intranasal (e.g., inhalation) routes of administration. Conjugate vaccine can be administered by bolus injection or by continuous infusion, as well as by localized administration, e.g., at a site of disease or injury. The conjugate vaccine can be optionally administered in a pharmaceutically or physiologically acceptable vehicle.

The term "vaccine" as used herein, is a broad term and is used in its ordinary sense, including, without limitation, conjugates of preferred embodiments or other antigens formulated with adjuvants, diluents, excipients, carriers, and other pharmaceutically acceptable substances. The term "pharmaceutically acceptable" is used to refer to a non-toxic material that is compatible with a biological system such as a cell, cell culture, tissue, or organism.

Immunization protocols for use with the conjugates of preferred embodiments provide compositions and methods for preventing or treating a disease, disorder and/or infection in a subject. The term "treating" as used herein, is a broad term and is used in its ordinary sense, including, without limitation, curative, preventative, prophylactic, palliative and/or ameliorative treatment.

The vaccine compositions are preferably sterile and contain either a therapeutically or prophylactically effective amount of the conjugate in a unit of weight or volume suitable for administration to a subject. The term "pharmaceutically-acceptable carrier" as used herein means one or more compatible solid or liquid filler, diluents or encapsulating substances which are suitable for administration into a subject. The term "carrier" denotes an organic or inorganic ingredient, natural or synthetic, with which the active ingredient is combined to facilitate the application. The characteristics of the carrier depend on the route of administration. Physiologically and pharmaceutically-acceptable carriers include diluents, fillers, salts, buffers, stabilizers, solubilizers, and other materials which are well known in the art.

The components of the pharmaceutical compositions also are capable of being co-mingled with the conjugates of the preferred embodiment, and with each other, in a manner such that there is no interaction which substantially impairs the desired pharmaceutical efficacy.

Formulation of the conjugate vaccines of preferred embodiments into pharmaceutical compositions can be accomplished using methods known in the art. The vaccine compositions can also contain one or more adjuvants. Suitable adjuvants include, for example, aluminum adjuvants, such as aluminum hydroxide or aluminum phosphate, Freund's Adjuvant, BAY, DC-chol, pcpp, monophosphoryl lipid A, CpG, QS-21, cholera toxin and formyl methionyl peptide. See, e.g., Vaccine Design, the Subunit and Adjuvant Approach, 1995 (M. F. Powell and M. J. Newman, eds., Plenum Press, N.Y.).

The dosage of conjugate vaccine to be administered a subject and the regime of administration can be determined in accordance with standard techniques well known to those of ordinary skill in the pharmaceutical and veterinary arts, taking into consideration such factors as the intended use, particular antigen, the adjuvant (if present), the age, sex, weight, species, general condition, prior illness and/or treatments, and the route of administration. Preliminary doses can be determined according to animal tests, and the scaling of dosages for human administration is performed according to art-accepted practices such as standard dosing trials. For example, the therapeutically effective dose can be estimated initially from serum antibody level testing. The dosage depends on the specific activity of the conjugate and can be readily determined by routine experimentation.

In practicing immunization protocols for treatment and/or prevention of specified diseases, a therapeutically effective amount of conjugate is administered to a subject. As used herein, the term "effective amount" means the total amount of therapeutic agent (e.g., conjugate) or other active component that is sufficient to show a meaningful benefit to the subject, such as, enhanced immune response, treatment, healing, prevention or amelioration of the relevant medical condition (disease, infection, or the like), or an increase in rate of treatment, healing, prevention or amelioration of such conditions. When "effective amount" is applied to an individual therapeutic agent administered alone, the term refers to that therapeutic agent alone. When applied to a combination, the term refers to combined amounts of the ingredients that result in the therapeutic effect, whether administered in combination, serially or simultaneously. As used herein, the phrase "administering an effective amount" of a therapeutic agent means that the subject is treated with said therapeutic agent(s) in an amount and for a time sufficient to induce an improvement, and preferably a sustained improvement, in at least one indicator that reflects the severity of the disease, infection, or disorder.

An improvement is considered "sustained" if the patient exhibits the improvement on at least two occasions separated by a period of time. The degree of improvement can be determined based, for example, on immunological data, or on signs or symptoms of a disease, infection, or disorder, Various indicators that reflect the extent of the patient's illness can be assessed for determining whether the amount and time of the treatment is sufficient. The baseline value for the chosen indicator or indicators can established based on by examination of the patient prior to administration of the first dose of the therapeutic agent, or based on statistical values generated from a population of healthy patients. If the therapeutic agent is administered to treat acute symptoms, the first dose is administered as soon as practically possible. Improvement is induced by administering therapeutic agents until the subject manifests an improvement over baseline for the chosen indicator or indicators. In treating chronic conditions, this degree of improvement is obtained by repeatedly administering the therapeutic agents over a period time, e.g., for one, two, or three months or longer, or indefinitely. A single dose can be sufficient for treating or preventing certain conditions. Treatment can be continued indefinitely at the same level or at a reduced dose or frequency, regardless of the patient's condition, if desired. Once treatment has been reduced or discontinued, it later can be resumed at the original level if symptoms reappear.

Generally, the amount of conjugate that provides an efficacious dose or therapeutically effective dose for vaccination against bacterial infection is from about 1 μg or less to about 100 μg or more, preferably from about 2, 3, 4, 5, 6, 7, 8, 9, 10, 15, 20, 25, 30, 35, 40, 45 or 50 μg to about 55, 60, 65, 70, 75, 80, 85, 90, or 95 μg per kg body weight. An efficacious dosage can require less antibody if the post-infection time elapsed is less, since there is less time for the bacteria to proliferate. An efficacious dosage can also depend on the bacterial load at the time of diagnosis. Multiple injections administered over a period of days can be considered for therapeutic usage.

The conjugate vaccines can be administered as a single dose or in a series including one or more boosters. For example, an infant or child can receive a single dose early in life, then be administered a booster dose up to 1, 2, 3, 4, 5, 6, 7, 8, 9, 10 or more years later. The booster dose generates antibodies from primed B-cells, i.e., an anamnestic response. That is, the conjugate vaccine elicits a high primary functional antibody response in infants or children, and is capable of eliciting an anamnestic response following a booster administration, demonstrating that the protective immune response elicited by the conjugate vaccine is long-lived.

The conjugate vaccines can be formulated into liquid preparations for, e.g., oral, nasal, anal, rectal, buccal, vaginal, peroral, intragastric, mucosal, perlinqual, alveolar, gingival, olfactory, or respiratory mucosa administration. Suitable forms for such administration include suspensions, syrups, and elixirs. The conjugate vaccines can also be formulated for parenteral, subcutaneous, intradermal, intramuscular, intraperitoneal or intravenous administration, injectable administration, sustained release from implants, or administration by eye drops. Suitable forms for such administration include sterile suspensions and emulsions. Such conjugate vaccines can be in admixture with a suitable carrier, diluent, or excipient such as sterile water, physiological saline, glucose, and the like. The conjugate vaccines can also be lyophilized. The conjugate vaccines can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "Remington: The Science and Practice of Pharmacy", Lippincott Williams & Wilkins; 20th edition (Jun. 1, 2003) and "Remington's Pharmaceutical Sciences", Mack Pub. Co.; $18^{th}$ and $19^{th}$ editions (December 1985, and June 1990, respectively), incorporated herein by reference in their entirety, can be consulted to prepare suitable preparations, without undue experimentation. Such preparations can include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. The presence of such additional components can influence the physical state, solubility, stability, rate of in vivo release, and rate of in vivo clearance, and are thus chosen according to the intended application, such that the characteristics of the carrier are tailored to the selected route of administration.

The conjugate vaccines are preferably provided as liquid suspensions or as freeze-dried products. Suitable liquid preparations include, e.g., isotonic aqueous solutions, suspensions, emulsions, or viscous compositions that are buffered to a selected pH. Transdermal preparations include lotions, gels, sprays, ointments or other suitable techniques. If nasal or respiratory (mucosal) administration is desired (e.g., aerosol inhalation or insufflation), compositions can be in a form and dispensed by a squeeze spray dispenser, pump dispenser or aerosol dispenser. Aerosols are usually under pressure by means of a hydrocarbon. Pump dispensers can preferably dispense a metered dose or a dose having a particular particle size, as discussed below.

When in the form of solutions, suspensions and gels, formulations of the conjugate can typically contain a major amount of water (preferably purified water) in addition to the active ingredient. Minor amounts of other ingredients such as pH adjusters, emulsifiers, dispersing agents, buffering agents, preservatives, wetting agents, jelling agents, colors, and the like can also be present.

The compositions are preferably isotonic with the blood or other body fluid of the recipient. The isotonicity of the compositions can be attained using sodium tartrate, propylene glycol or other inorganic or organic solutes. Sodium chloride is particularly preferred. Buffering agents can be employed, such as acetic acid and salts, citric acid and salts, boric acid and salts, and phosphoric acid and salts. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like.

Viscosity of the compositions can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener can depend upon the agent selected. The important point is to use an amount that can achieve the selected viscosity. Viscous compositions are normally prepared from solutions by the addition of such thickening agents.

A pharmaceutically acceptable preservative can be employed to increase the shelf life of the compositions. Benzyl alcohol can be suitable, although a variety of preservatives including, for example, parabens, thimerosal, chlorobutanol, or benzalkonium chloride can also be employed. A suitable concentration of the preservative can be from 0.02% to 2% based on the total weight although there can be appreciable variation depending upon the agent selected.

Pulmonary delivery of the conjugate can also be employed. The conjugate is delivered to the lungs of a mammal while inhaling and traverses across the lung epithelial lining to the blood stream. A wide range of mechanical devices designed for pulmonary delivery of therapeutic products can be employed, including but not limited to nebulizers, metered dose inhalers, and powder inhalers, all of which are familiar to those skilled in the art. These devices employ formulations suitable for the dispensing of the conjugate. Typically, each formulation is specific to the type of device employed and can involve the use of an appropriate propellant material, in addition to diluents, adjuvants and/or carriers useful in therapy.

The conjugate is advantageously prepared for pulmonary delivery in particulate form with an average particle size of from 0.1 μm or less to 10 μm or more, more preferably from about 0.2, 0.3, 0.4, 0.5, 0.6, 0.7, 0.8, or 0.9 μm to about 1.0, 1.5, 2.0, 2.5, 3.0, 3.5, 4.0, 4.5, 5.0, 5.5, 6.0, 6.5, 7.0, 7.5, 8.0, 8.5, 9.0, or 9.5 μm for pulmonary delivery. Pharmaceutically acceptable carriers for pulmonary delivery of the conjugates include carbohydrates such as trehalose, mannitol, xylitol, sucrose, lactose, and sorbitol. Other ingredients for use in formulations can include DPPC, DOPE, DSPC and DOPC. Natural or synthetic surfactants can be used, including polyethylene glycol and dextrans, such as cyclodextran. Bile salts and other related enhancers, as well as cellulose and cellulose derivatives, and amino acids can also be used. Liposomes, microcapsules, microspheres, inclusion complexes, and other types of carriers can also be employed.

Formulations suitable for use with a nebulizer, either jet or ultrasonic, typically comprise the conjugate dissolved or suspended in water at a concentration of about 0.01 or less to 100 mg or more of conjugate per mL of solution, preferably from about 0.1, 1, 2, 3, 4, 5, 6, 7, 8, 9, or 10 mg to about 15, 20, 25, 30, 35, 40, 45, 50, 55, 60, 65, 70, 75, 80, 85, or 90 mg of conjugate per mL of solution. The formulation can also include a buffer and a simple sugar (erg., for protein stabilization and regulation of osmotic pressure). The nebulizer formulation can also contain a surfactant, to reduce or prevent surface induced aggregation of the conjugate caused by atomization of the solution in forming the aerosol.

Formulations for use with a metered-dose inhaler device generally comprise a finely divided powder containing the inventive compound suspended in a propellant with the aid of a surfactant. The propellant can include conventional propellants, such chlorofluorocarbon, a hydrochlorofluorocarbons, hydrofluorocarbons, and hydrocarbons, such as trichlorofluoromethane, dichlorodifluoromethane, dichlorotetrafluoroethanol, and 1,1,1,2-tetrafluoroethane, and combinations thereof. Suitable surfactants include sorbitan trioleate, soya lecithin, and oleic acid.

Formulations for dispensing from a powder inhaler device typically comprise a finely divided dry powder containing the conjugate, optionally including a bulking agent, such as lactose, sorbitol, sucrose, mannitol, trehalose, or xylitol in an amount that facilitates dispersal of the powder from the device, typically from about 1 wt. % or less to 99 wt. % or more of the formulation, preferably from about 5, 10, 15, 20, 25, 30, 35, 40, 45, or 50 wt. % to about 55, 60, 65, 70, 75, 80, 85, or 90 wt. % of the formulation.

When the conjugate is administered by intravenous, cutaneous, subcutaneous, or other injection, the conjugate vaccine is preferably in the form of a pyrogen-free, parenterally acceptable aqueous solution. The preparation of parenterally acceptable solutions with suitable pH, isotonicity, stability, and the like, is within the skill in the art. A preferred pharmaceutical composition for injection preferably contains an isotonic vehicle such as Sodium Chloride Injection, Ringer's Injection, Dextrose Injection, Dextrose and Sodium Chloride Injection, Lactated Ringer's Injection, or other vehicles as are known in the art. The pharmaceutical compositions can also contain stabilizers, preservatives, buffers, antioxidants, or other additives known to those of skill in the art.

The duration of the injection can vary depending upon various factors, and can comprise a single injection administered over the course of a few seconds or less, to 1, 2, 3, 4, 5, 6, 7, 8, 9, 10, 11, 12, 13, 14, 15, 16, 17, 1 8, 19, 20, 21, 22, 23, or 24 hours or more of continuous intravenous administration.

The conjugate can be administered topically, systematically, or locally, via a liquid or gel, or as an implant or device The conjugates of preferred embodiments, or the conjugation methods of preferred embodiments, can be useful in preparing vaccines for the treatment of a variety of bacterial infections, including infections by *Helicobacter pyloris, Borelia burgdorferi, Legionella pneumophilia, Mycobacteria* sps. (e.g. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridatis* group), *Streptococcus faecalis, Streptococcus bovis, Streptococcus* (*anaerobic* sps.), *Streptococcus pneumoniae, pathogenic Campylobacter* sp., *Enterococcus* sp., *Haemophilus influenzae, Bacillus anthracis, Corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema palladium, Treponema pertenue, Leptospira*, and *Actinomyces israelli.*

Certain methods of the preferred embodiments can also be of use in preparing vaccines for treating or vaccinating subjects against cancer, such as mammalian sarcomas and carcinomas, such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, serminoma, embryonal carcinoma, Wilms' tumor, cervical cancer, testicular tumor, lung carcinoma, small cell lung carcinoma, bladder carcinoma, epitbelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, such as acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease, lymphoproliferative disorders including autoimmune lymphoproliferative syndrome (ALPS), chronic lymphoblastic leukemia, hairy cell leukemia, chronic lymphatic leukemia, peripheral T-cell lymphoma, small lymphocytic lymphoma, mantle cell lymphoma, follicular lymphoma, Burkitt's lymphoma, Epstein-Barr virus-positive T cell lymphoma, histiocytic lymphoma, Hodgkin's disease, diffuse aggressive lymphoma, acute lymphatic leukemias, T gamma lymphoproliferative disease, cutaneous B cell lymphorma, cutaneous T cell lymphoma (i.e., mycosis fungoides) and Szary syndrome.

The conjugates can be administered in combination with various vaccines either currently being used or in development, whether intended for human or non-human subjects. Examples of vaccines for human subjects and directed to infectious diseases include the combined diphtheria and tetanus toxoids vaccine; pertussis whole cell vaccine; the inactivated influenza vaccine; the 23-valent pneumococcal vaccine; the live measles vaccine; the live mumps vaccine; live rubella vaccine; Bacille Calmette-Guerin (BCG) tuberculosis vaccine; hepatitis A vaccine; hepatitis B vaccine; hepatitis C vaccine; rabies vaccine (e.g., human diploid cell vaccine); inactivated polio vaccine; meningococcal polysaccharide vaccine; quadrivalent meningococcal vaccine; yellow fever live virus vaccine; typhoid killed whole cell vaccine; cholera vaccine; Japanese B encephalitis killed virus vaccine; adenovirus vaccine; cytomegalovirus vaccine; rotavirus vaccine; varicella vaccine; anthrax vaccine; small pox vaccine; and other commercially available and experimental vaccines.

The conjugates can be provided to an administering physician or other health care professional in the form of a kit. The kit is a package which houses a container which contains the conjugate vaccine and instructions for administering the conjugate vaccine to a subject. The kit can optionally also contain one or more other therapeutic agents. The kit can optionally contain one or more diagnostic tools and instructions for use. For example, a vaccine cocktail containing two or more vaccines can be included, or separate pharmaceutical compositions containing different vaccines or therapeutic agents. The kit can also contain separate doses of the conjugate vaccine for serial or sequential administration. The kit can contain suitable delivery devices, e.g., syringes, inhalation devices, and the like, along with instructions for administrating the therapeutic agents. The kit can optionally contain instructions for storage, reconstitution (if applicable), and administration of any or all therapeutic agents included. The kits can include a plurality of containers reflecting the number of administrations to be given to a subject. If the kit contains a first and second container, then a plurality of these can be present.

EXPERIMENTS

Materials

Tetanus toxoid (TT) was provided by Instituto Butantan, Sao Paulo, SP, Brazil. It was produced and purified accordingly the specifications required to DTP vaccine application (World Health Organization, 1990, Requirements for diphtheria, tetanus, pertussis and combined vaccines, WHO Technical report series N°. 800, Geneva, World Health Organization). The antigenic purity of TT is higher than 1,500 Lf/mg protein Nitrogen (World Health Organization Expert Committee on Biological standardization, 2001. Recommendations for the production & control of meningococcal group C conjugate vaccines (Draft), Geneva, 26-30 November). The protein content was evaluated by Bradford's method. See Bradford, M. M. 1976, Anal. Biochem., 72:248.

Meningococcal groups A and C polysaccharides (Mn A PS and Mn C PS, respectively) were provided by Bio-Manguinhos, Fundação Oswaldo Cruz, Rio de Janeiro, R J, Brasil. They were obtained by cultivation of *N. meningitidis* 1951 and 2135 vaccinal strains, respectively, in Frantz medium and purified as described previously. Briefly, the cultures were harvested after killing the microorganisms by heating at 56° C. for 30 minutes, after which the APS and CPS were partially purified by precipitation with hexadecyl trimethylammonium bromide (Cetavlon). The cetavlon-precipitated capsular polysaccharides were purified by phenol extraction followed by endotoxin elimination by differential centrifugation (Gotschlich et al., 1969, J.Exp. Med., 129:1349-1365; World Health Organization, 1976, Requirements for meningococcal polysaccharide vaccine. Technical report series, N°. 594, 50-75, Geneva; World Health Organization, 1981, Requirements for meningococcal polysaccharide vaccine. Technical report series, N°. 658, Geneva, World Health Organization 29).

The sugar content of CPS and APS was measured by Svennerholm's method and high-performance anion-exchange chromatography with pulsed-amperometric detection (HPAEC-PAD), respectively (Svennerholm, L. 1957, Biochim. Biophys. Acta, 24:604-611; Ricci et al., 2001, Vaccine, 19:1989-1997). The polysaccharides identities, structures, and purities were evaluated by Proton Nuclear Magnetic Resonance (NMR) (Jones et al. 1996, Dev. Biol. Stand. Basel Karger, 87:143-151; Jodar et al., 2004, Vaccine, 22:1047-1053).

Methods

Protein Activation

TT was activated with hydrazine dihydrochloride in 50× excess to introduce hydrazine groups via carbodiimide methodology at room temperature and acidic conditions. The hydrazine activated tetanus toxoid (TTH) obtained was purified by diafiltration against 0.02M PBS pH 7.4 (~12 volumes) and concentrated using a Tangential Flow Ultrafiltration (Minisette System—Pall BioPharmaceuticals) and membranes cassettes type Omega (Screen Channel—Hydrophilic polyethersulphone) (Handbook, 1999). The purification conditions were standardized to process at least 5 liters of solution.

Conjugation

Hydrazine-activated TT (TTH) was reacted with aldehyde-activated polysaccharide at ratio from 1:1.6 to 1:5 and concentration range 1-40 mg/mL overnight, pH 5.0-7.0, 22-45° C. in presence of 1N sodium cyanoborohydride. Adipic acid dihydrazide (ADH) was then added for 3h to neutralize unreacted aldehyde groups. The solutions were diafiltrated against 0.02M PBS pH 7.4 (~20 volumes), to remove unreacted compounds and unconjugated polysaccharides, then concentrated using a Tangential Flow Ultrafiltration (Minisette System—Pall BioPharmaceuticals) and membrane cassettes type Omega (Screen Channel—Hydrophilic polyethersulphone) (Handbook, 1999). The methodology of purification was standardized to process volumes above 2 liters of mixture.

Preparation of Bulk Product

The final bulk was prepared by mixing saccharose as stabilizer with a suitable quantity of the bulk conjugate in order to obtain 5 human doses vials (10 μg/0.5 mL) in sterile conditions.

The product was freezed below the eutectic point. After completion of the sublimation phase, the product temperature was gradatively raised. The final residual moisture (1%) was determined through a moisture test (pressure-differential technique) and Nitrogen Bath, this last conducted at the end of the drying phase. From a cosmetic point of view, the cycle yielded a white homogenous dried cake, demonstrating a satisfactory result.

Quality Control of Vaccines—Physico-Chemical Assays

High performance liquid size-exclusion chromatography (HPSEC) analysis of samples of proteins, polysaccharides and conjugate products (50 μL; 0.1-1 mg/mL) were conducted using a TSK 4,000 $P_{wxl}$ column with saline at 0.5 mL/minute in an Amerscham Biosciences HPLC system with the software Unicom 4.12 and a UV detector at 280 and 206 nm, to detect protein and sugar signals, respectively.

Total protein and polysaccharide contents in the product intermediates and the final conjugates were determined by Bradford's method and resorcinol and HPAEC-PAD assays, respectively (see Svennerholm, L. 1957, Biochim. Biophys. Acta, 24:604-611; Bradford, M. M. 1976, Anal. Biochem., 72:248; Ricci et al., 2001, Vaccine, 19:1989-1997). The results for CPS were used to calculate the ratios of saccharide to protein obtained for different conjugate batches (Table 3). This parameter was employed to evaluate consistency of production.

TABLE 3

Saccharide-protein ratios (w/w) of three different Men C conjugates

| Conjugate (lots) | Ratio sugar:protein | Dose (10 μg/dose) |
|---|---|---|
| 28 | 1:2.12 | 2665 |
| 29 | 1:2.04 | 2000 |
| 30 | 1:2.35 | 2028 |

The amine groups amount present in the TTH was measured by TNBSA assay using glycine as standard (Pierce Instructions for TNBSA assay).

The native APS and CPS identities/structures and purities were evaluated by +HNMR. Samples dissolved in $D_2O$ (~10 mg/nL) plus 0.01% dimethyl sulfoxide (DMSO) (used as a internal standard) were run at 600 MHz and 40° C. The aldehyde groups present in the activated-polysaccharides and the conjugation step were also monitored by +HNMR using the same conditions without 0.01% DMSO in the solvent (Egan, W. 2000, Dev. Biol. Base, Karger, 103:3-9).

The molecular weight of native and oxidized polysaccharides and conjugates were determined by "Multi-Angle Laser Light Scattering" (MALLS) using a concentration range (0.025-0.4 mg/mL) in 0.4M KCl/0.05M sodium acetate (see Jumel et al, 2002, Biotechnol. Appl. Biochem., 36:219-226).

The unbound or free polysaccharide in the purified bulk conjugate was assayed by different methods, for example, ultrafiltration, in order to ensure that the amount present is clinically safe and efficacious (see World Health Organization Expert Committee on Biological standardization. 2001. Recommendations for the production & control of meningococcal group C conjugate vaccines (Draft). Geneva, 26-30 November; Jodar et al., 2004, Vaccine, 22:1047-1053).

The saccharose amount present in lyophilized conjugate vaccine was evaluated by HPAEC-PAD (see World Health Organization Expert Committee on Biological standardization. 2001. Recommendations for the production & control of meningococcal group C conjugate vaccines (Draft). Geneva, 26-30 Nov.).

The purified bulks conjugate was tested for bacterial and mycotic sterility in accordance with the WHO requirements (see World Health Organization Expert Committee on Biological standardization. 2001. Recommendations for the production & control of meningococcal group C conjugate vaccines (Draft). Geneva, 26-30 Nov.).

The residual moisture of lyophilized conjugate vaccines was measured by Karl Fischer methodology (Wieland, G. 1987. Water determination by Karl Fischer Titration. Theory and Applications. Printed by Git Verlag GMBH, Germany.). The average content is preferably no greater than 2.5%.

The pyrogen content of lyophilized conjugate vaccines was determined "in vitro" and "in vivo" by *Limulus ainoebocyte* lysate (LAL; less than 100 International Units of endotoxin per g of polysaccharide) and pyrogenicity test in rabbits, respectively (see World Health Organization Expert Committee on Biological standardization. 2001. Recommendations for the production & control of meningococcal group C conjugate vaccines (Draft). Geneva, 26-30 Nov.).

Chromatographic Analysis of Meningococcal Group A Native and Oxidized Polysaccharides and Polysaccharide-Protein Conjugate In order to control the process of the conjugation step, samples of activated Tetanus Toxoid, oxidized polysaccharide, and conjugate products (50 μL; 0.1-1 mg/mL) were eluted in a TSK 4,000 $P_{wxl}$ column with saline at 0.5 mL/minute in a Amerscham Biosciences HPLC system with the software Unicorn 4.12 and a UV detector at 280 and 206 nm, to detect protein and sugar signals, respectively (FIG. 1).

Immunogenicity of Meningococcal Group C Polysaccharide-Protein Conjugates in Mice Swiss mice (15-22 g; groups of 10) were immunized intramuscularly with 2 μg/dose (0.2 mL) of plain polysaccharide or polysaccharide-protein conjugates (three different lots) on days 0, 21 and 41. Antiserum was collected before each dose and 14 days after the third dose and assayed by ELISA for total IgG titers against polysaccharide. The immunized groups were compared with a control group, which received PBS in the same volume.

Figure 2:
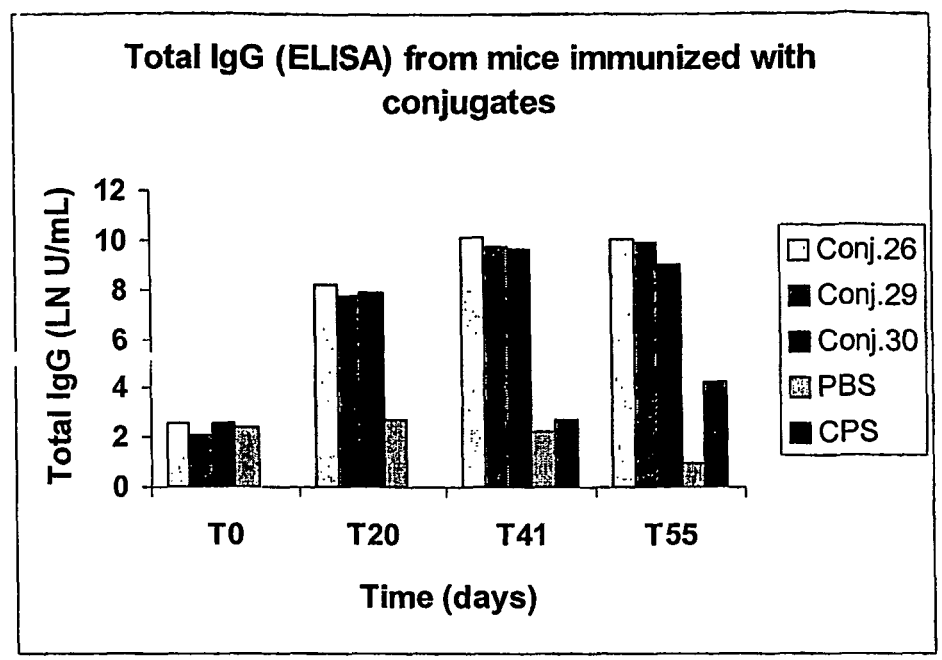
FIG. 2 provides total IgG (ELISA) from mice immunized with 3 doses of three different Men C conjugates (21 days apart).

ELISA assays were conducted. Immulon plates type II (Dynex) were coated with 100 μL coating solution-containing polysaccharide admixed with methylated human serum albumin overnight. After washing four times with 200 μL washing buffer (PBS with 0.05% Tween 20, 0.05% $NaN_3$), 100 μL of antiserum samples and standard serum at a serial two-fold dilution starting from 1/5000 (diluted with dilution buffer containing PBS, 4% newborn calf serum, 0.05% NaN$_3$) were added to each well. After overnight incubation, the plates were washed four times and incubated with 100 µL goat anti-mouse IgG whole molecule conjugated with alkaline phosphate (1/3000 dilution in dilution buffer) for two hours. After washing (4×200 µL), the plates were incubated with 100 µL p-nitrophenyl phosphate (1 mg/mL) for 30 minutes and the reaction was stopped with 50 µL 0.1N NaOH (see Gheesling et al., 1994, J. Clin. Microbiol., 32: 1475-1482). The ELISA readings were measured with a plate reader (405 nm) and the anti-polysaccharide antibody levels of the antiserum samples were calculated from the ELISA readings and the standard curve of the standard serum co-assayed in the same plate. The geometric mean of antibody level for each mouse group was calculated (FIG. 2).

Figure 3:
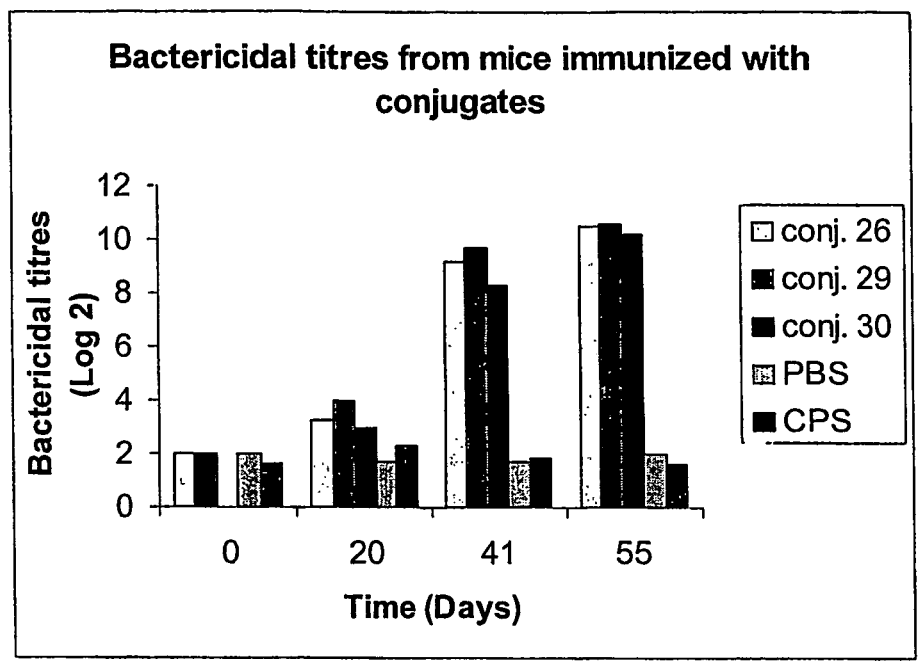
FIG. 3 provides bactericidal titres from mice immunized with 3 doses of three different Men C conjugates (21 days apart) (target strain *N. meningitidis* C).

Serum bactericidal activity was determined. Two-fold dilutions of sera were tested with an inoculum of 50-70 cfu per well of log phase meningococcal grown on Tryptic Soy Agar (TSA). Serum obtained from male guinea pigs was used as the source of complement (free of bactericidal antibodies to *N. meningitidis* serogroup C). The assay was carried out at 37° C. for 30 minutes, and 150 µl of TSA with 2% BSA was added to each well. Quantitative cultures were performed at time 0 and 30 minutes later by the tilt method in duplicate. The bactericidal antibody titres were expressed as log2 of the final dilution that yields at least 50% killing of the inoculum (see Milagres et al., 1994, Infect. Inmun.; 62 (10):4419-24) (FIG. 3).

Discussion

The steps described above were demonstrated effective in producing, purifying, and controlling Men A and C conjugate vaccines in commercial quantities. Using the methods described above, different lots of conjugates were prepared by reductive amination in industrial scale production to yield large volumes of final product. The downstream procedure optimizes the steps of purification using tangential filtration in order to get good yields of soluble products without free polysaccharides. The established production procedures were reproducible. The physico-chemical quality controls and immunogenic evaluation for Men C were consistent for the three final lots obtained, indicating that the developed vaccines are suitable for testing in phase 1 clinical studies.

The procedures described above can be applied to production of other conjugate vaccines against different encapsulated bacteria with appropriate adaptations.

All references cited herein are incorporated herein by reference in their entirety. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that can vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims.

What is claimed is:

1. A method for preparing a meningococcal-tetanus toxoid conjugate vaccine in commercial volumes, the method comprising: reacting a meningococcal polysaccharide with an oxidizing agent, whereby a solution of an aldehyde-activated meningococcal polysaccharide is obtained; reacting a tetanus toxoid protein with hydrazine dichloride at an acidic pH, whereby a solution of a hydrazine-activated tetanus toxoid protein is obtained; purifying by diafiltration said solution of hydrazine-activated tetanus toxoid protein to process at least five liters of solution; reacting the aldehyde-activated meningococcal polysaccharide with the hydrazine- activated tetanus toxoid protein at a pH of from 5 to 7 in the presence of sodium cyanoborohydride, whereby a meningococcal-tetanus toxoid conjugate is obtained; neutralizing unreacted aldehyde groups with adipic acid dihydrazide; purifying by diafiltration the resulting solution to process a volume of at least two liters, producing a purified meningococcal-tetanus toxoid conjugate vaccine, and concentrating the purified meningococcal-tetanus toxoid conjugate vaccine by tangential flow ultrafiltration, yielding a concentrated purified meningococcal-tetanus toxoid conjugate vaccine, whereby the meningococcal-tetanus toxoid conjugate vaccine capable of stimulating an immune response is obtained in commercial volumes.

2. The method according to claim 1, wherein the oxidizing agent comprises NaIO$_4$.

3. The method according to claim 1, wherein the solution of the aldehyde-activated meningococcal polysaccharide is buffer exchanged with a HEPES buffer.

4. The method according to claim 1, wherein the solution of the aldehyde-activated meningococcal polysaccharide is buffer exchanged to a pH from 7 to 8.

5. The method according to claim 1, wherein the solution of the hydrazine-activated tetanus toxoid protein is buffer exchanged with a Na$_2$CO$_3$ buffer.

6. The method according to claim 1, wherein the solution of the hydrazine-activated tetanus toxoid protein is buffer exchanged to a pH from 10.0 to 11.0.

7. The method according to claim 6, wherein a pH of the solution of the hydrazine-activated tetanus toxoid protein is raised from 7.0 to 11 before the solution of the hydrazine-activated tetanus toxoid protein is buffer exchanged to a pH from 10.0 to 11.0.

8. The method according to claim 1, wherein the aldehyde-activated meningococcal polysaccharide is reacted with the hydrazine-activated tetanus toxoid protein at a ratio from 1:1.6 to 1:5.

9. The method according to claim 1, wherein said purifying the resulting solution comprises the step of diafiltrating the meningococcal-tetanus toxoid conjugate vaccine, whereby unreacted compounds and unconjugated meningococcal polysaccharides are removed, yielding a purified meningococcal-tetanus toxoid conjugate vaccine.

10. The method according to claim 1, further comprising the step of adding saccharose as a stabilizer to the concentrated purified meningococcal-tetanus toxoid conjugate vaccine, yielding a stabilized meningococcal-tetanus toxoid conjugate vaccine.

11. The method according to claim 1, further comprising the step of freeze drying the concentrated purified meningococcal-tetanus toxoid conjugate vaccine, yielding a dried meningococcal-tetanus toxoid conjugate vaccine.

12. A method for preparing a meningococcal-tetanus toxoid conjugate vaccine in commercial volumes, the method comprising: reacting a meningococcal polysaccharide with an oxidizing agent, whereby a solution of an aldehyde-activated meningococcal polysaccharide is obtained; buffer exchanging the solution of the aldehyde-activated meningococcal polysaccharide to a pH from about 7 to 8; reacting a tetanus toxoid protein with hydrazine dichloride at an acidic pH, whereby a solution of a hydrazine-activated tetanus toxoid protein is obtained; raising a pH of the solution of the hydrazine-activated tetanus toxoid protein from 7.0 to 11 and thereafter buffer exchanging the solution of the hydrazine-activated tetanus toxoid protein to a pH from 10.0 to 11.0; purifying by diafiltration said solution of hydrazine-activated tetanus toxoid protein to process at least five liters of solution; reacting the aldehyde-activated meningococcal polysaccharide with the hydrazine-activated tetanus toxoid protein at a pH from 5 to 7 in the presence of sodium cyanoborohydride, whereby a meningococcal-tetanus toxoid conjugate is obtained; neutralizing unreacted aldehyde groups with adipic acid dihydrazide; purifying by diafiltration the resulting solution to process a volume of at least two liters, producing a purified meningococcal-tetanus toxoid conjugate vaccine, and concentrating the purified meningococcal-tetanus toxoid conjugate vaccine by tangential flow ultrafiltration, yielding a concentrated purified meningococcal-tetanus toxoid conjugate vaccine, whereby a meningococcal-tetanus toxoid conjugate vaccine capable of stimulating an immune response is obtained in commercial volumes.

13. The method according to claim 12, wherein the aldehyde-activated meningococcal polysaccharide is reacted with the hydrazine-activated tetanus toxoid protein at a ratio from 1:1.6 to 1:5.

14. The method according to claim 12, further comprising the step of adding saccharose as a stabilizer to the concentrated purified meningococcal-tetanus toxoid conjugate vaccine, yielding a stabilized meningococcal-tetanus toxoid conjugate vaccine.

\* \* \* \* \*